(12) United States Patent
Kawai

(10) Patent No.: US 10,842,435 B2
(45) Date of Patent: Nov. 24, 2020

(54) CONTACT-TYPE SENSOR

(71) Applicant: OMRON Corporation, Kyoto (JP)

(72) Inventor: Wakahiro Kawai, Konan (JP)

(73) Assignee: OMRON Corporation, Kyoto (JP)

( * ) Notice: Subject to any disclaimer, the term of this patent is extended or adjusted under 35 U.S.C. 154(b) by 402 days.

(21) Appl. No.: 15/736,781

(22) PCT Filed: Aug. 23, 2016

(86) PCT No.: PCT/JP2016/074436
§ 371 (c)(1),
(2) Date: Dec. 15, 2017

(87) PCT Pub. No.: WO2017/056785
PCT Pub. Date: Apr. 6, 2017

(65) Prior Publication Data
US 2018/0168505 A1     Jun. 21, 2018

(30) Foreign Application Priority Data
Sep. 30, 2015 (JP) .................. 2015-193423

(51) Int. Cl.
*A61B 5/00* (2006.01)
*A61B 5/01* (2006.01)
(Continued)

(52) U.S. Cl.
CPC .............. *A61B 5/6801* (2013.01); *A61B 5/01* (2013.01); *A61B 5/4266* (2013.01);
(Continued)

(58) Field of Classification Search
CPC ..... A61B 65/4801; A61B 5/01; A61B 5/4277; A61B 5/6833; A61B 5/6801;
(Continued)

(56) References Cited

U.S. PATENT DOCUMENTS

| 5,232,284 A * | 8/1993 | Egawa ...................... G01J 5/02 |
| | | 374/126 |
| 2005/0141591 A1 | 6/2005 | Sakano |

(Continued)

FOREIGN PATENT DOCUMENTS

| CN | 1428599 | 7/2003 |
| CN | 104758123 | 7/2015 |

(Continued)

OTHER PUBLICATIONS

"Search Report of Europe Counterpart Application", dated Jun. 3, 2019, p. 1-p. 7.

(Continued)

*Primary Examiner* — David J. McCrosky
*Assistant Examiner* — Chanel J Jhin
(74) *Attorney, Agent, or Firm* — JCIPRNET

(57) ABSTRACT

The present invention limits measurement error and sensor element damage. When a contact-type sensor (200) is placed in contact with skin (10), a gap (200*a*) is formed between the skin (10) and a sensor element (214). The contact-type sensor (200) is provided with a water-repellent resin base plate (212) and a water-absorbing sheet (211) that, together with the skin (10) and the sensor element (214), surround the gap (200*a*).

6 Claims, 4 Drawing Sheets

(51) Int. Cl.
  *G01J 5/02* (2006.01)
  *G01J 5/00* (2006.01)
  *G01J 5/12* (2006.01)
(52) U.S. Cl.
  CPC .......... *A61B 5/6833* (2013.01); *G01J 5/0025* (2013.01); *G01J 5/0285* (2013.01); *G01J 5/12* (2013.01); *B32B 2307/7265* (2013.01)
(58) Field of Classification Search
  CPC .............. A61B 5/4266; A61B 5/14517; A61B 5/14521; A61B 5/14507; A61B 5/68335; G01J 5/0025; G01J 5/0285; G01J 5/12; B32B 2307/7265
  USPC .......................................... 600/549, 346, 474
  See application file for complete search history.

(56) References Cited

U.S. PATENT DOCUMENTS

2011/0054283 A1   3/2011   Shuler
2016/0058380 A1*  3/2016   Lee .................... A61B 5/68335
                                                    600/365

FOREIGN PATENT DOCUMENTS

| JP | H0951877 | 2/1997 |
| JP | 2003-270051 | 9/2003 |
| JP | 2007-319506 | 12/2007 |
| JP | 2012-085983 | 5/2012 |
| JP | 2013-090894 | 5/2013 |
| JP | 5359550 | 12/2013 |

OTHER PUBLICATIONS

Office Action of Korean Counterpart Application, with English translation thereof, dated Apr. 18, 2019, pp. 1-7.
"Office Action of China Counterpart Application," with English translation thereof, dated Dec. 3, 2019, p. 1-p. 14.
"International Search Report (Form PCT/ISA/210) of PCT/JP2016/074436," dated Nov. 29, 2016, with English translation thereof, pp. 1-2.
"Written Opinion of the International Searching Authority (Form PCT/ISA/237) of PCT/JP2016/074436," dated Nov. 29, 2016, with English translation thereof, pp. 1-8.

* cited by examiner

CONTACT-TYPE SENSOR

CROSS-REFERENCE TO RELATED APPLICATION

This application is a 371 application of the international PCT application serial no. PCT/JP2016/074436, filed on Aug. 23, 2016, which claims the priority benefit of Japan application no. 2015-193423, filed on Sep. 30, 2015. The entirety of each of the abovementioned patent applications is hereby incorporated by reference herein and made a part of this specification.

TECHNICAL FIELD

The present disclosure relates to a contact-type sensor which is adapted to perform measurement while being in contact with an object to be measured such as the skin of the body.

BACKGROUND ART

There is an increasing demand for contact-type sensors capable of constantly measuring body temperature or body surface humidity and perspiration. Contact-type sensors are aimed at prevention of hyperthermia such as sunstroke, thermal fatigue, heatstroke and so on, or early detection of diseases accompanied by high temperature fever such as influenza. The contact-type sensor is attached to a surface portion (the skin) of a human body and has a sensor element for performing measurement of a degree of perspiration or temperature, and it is thin, lightweight, compact, highly water resistant wearable electronic equipment.

Conventionally, as a contact-type sensor, a body perspiration monitoring apparatus proposed in Patent Literature 1 is known. FIG. 1 is a schematic diagram illustrating this body perspiration monitoring apparatus. As illustrated in FIG. 1, the body perspiration monitoring apparatus 110 includes a sensor element (temperature and humidity sensor) 114, a shielding plate 113 for controlling a flow of sweat vapor, and a case 116 designed to optimize sensor sensitivity and serving to measure a degree of perspiration from the skin 100.

Further, Patent Literature 2 proposes a warning apparatus which includes the components included in the body perspiration monitoring apparatus of Patent Literature 1 and a sensor element which captures heat dissipation over time and predicts the occurrence of hyperthermia.

LITERATURE LIST

Patent Literature

Patent Literature 1:
Japanese Unexamined Patent Application Publication No. 2012-85983
Patent Literature 2:
Japanese Unexamined Patent Application Publication No. 2013-90894
Patent Literature 3:
Japanese Patent No. 5359550

SUMMARY OF THE INVENTION

Technical Problem

In the apparatuses proposed in Patent Literatures 1 and 2, as illustrated in FIG. 1, an inflow hole 112 for introducing the sweat vapor discharged from the skin 100 is formed. Not only the sweat vapor but also a liquid (for example, sweat in a liquid state) may enter an inside of the apparatus from the inflow hole 112, and the liquid may adhere to the sensor element 114 in some cases. When liquid adheres to the sensor element 114, there may be certain problems such as measurement errors being likely to occur and the sensor element 114 also being easily damaged.

The present invention has been made in view of the above problems, and an object thereof is to prevent measurement errors and breakage in a sensor element in a contact-type sensor.

Solution to Problem

To solve the above-described problems, a contact-type sensor of the present invention includes a contact portion which is brought into contact with an object to be measured, a sensor element which is disposed with a gap between the sensor element and the object to be measured and detects a detection target generated from the object to be measured when the contact portion is in contact with the object to be measured, and a water repellent portion and a water absorbing portion which surrounds the gap together with the object to be measured and the sensor element when the contact portion is in contact with the object to be measured.

Advantageous Effects of Invention

An object of the present invention is to suppress the measurement error and the breakage of the sensor element in the contact-type sensor.

DESCRIPTION OF THE EMBODIMENTS

Hereinafter, a contact-type sensor according to an embodiment of the present invention will be described with reference to the drawings. FIG. 2(*a*) is a front view schematically illustrating a contact-type sensor according to one embodiment of the present invention, and FIG. 2(*b*) is a view schematically illustrating a cross section taken along line A-A of the contact-type sensor of FIG. 2(*a*).

The contact-type sensor 200 of the embodiment is used by being brought into contact with the skin (body surface) 10 of a person as an object to be measured and is an electronic device which detects a body temperature of the person with a thermopile installed therein. Further, in the embodiment, as illustrated in FIG. 2(*b*), in the contact-type sensor 200, a side thereof which is brought into contact with the skin 10 is a front surface, and a side thereof opposite to the side in contact with the skin 10 is a rear surface.

Figure 1:
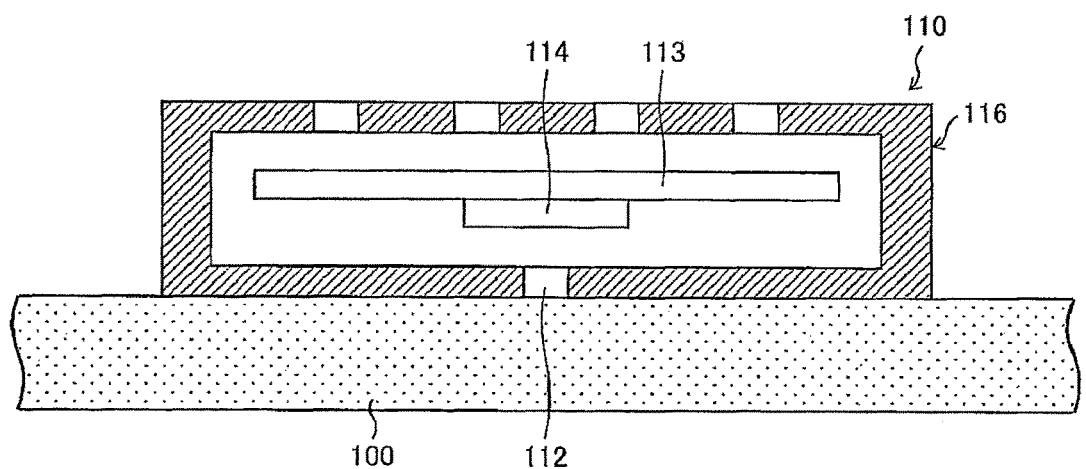
FIG. 1 is a schematic diagram illustrating a conventional body perspiration monitoring apparatus.
Figures 2A, 2B:
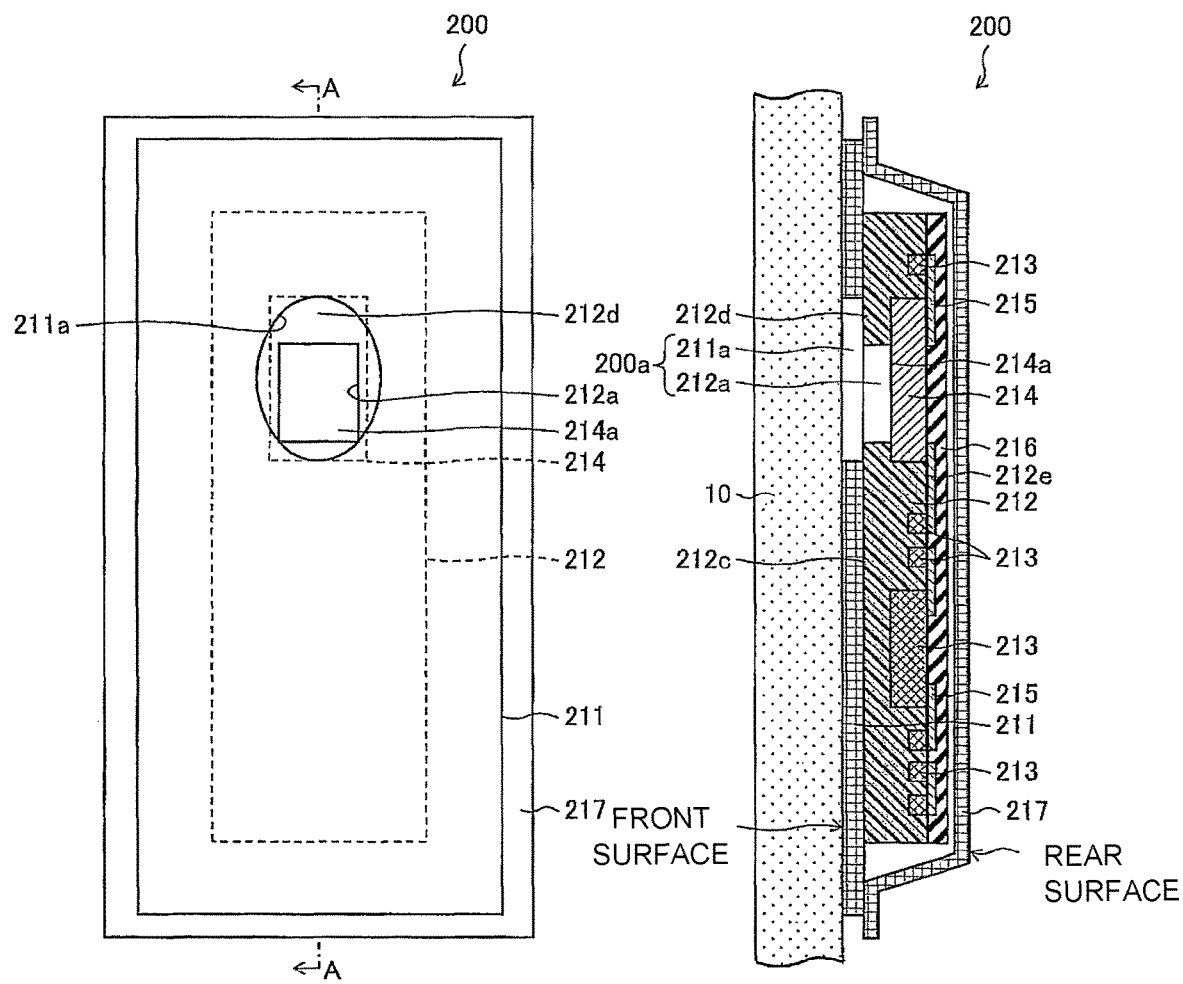
FIG. 2(*a*) and FIG. 2(*b*) are respectively a front view and a cross-sectional view of a contact-type sensor according to an embodiment of the present invention.

As illustrated in FIG. 2(a) and FIG. 2(b), the contact-type sensor 200 includes a water absorptive sheet 211, a resin substrate (casing) 212, electronic components 213, a sensor element 214, wiring 215, an insulating layer 216 and a hygroscopic sheet 217.

In the contact-type sensor 200, the water absorptive sheet 211, the resin substrate 212, the wiring 215, the insulating layer 216 and the hygroscopic sheet 217, respectively in a direction from the front surface side toward the rear surface side are arranged parallel to each other, and the electronic components 213 and the sensor element 214 are embedded in the resin substrate 212.

The resin substrate 212 is a member having a substantially flat plate shape and is formed of a resin, and the electronic component 213 and the sensor element 214 are embedded and supported therein. Further, in the embodiment, a surface of the resin substrate 212 facing the water absorptive sheet 211 is defined as a substrate front surface 212c, and a surface thereof opposite to the substrate front surface 212c is defined as a substrate rear surface 212e.

The electronic component 213 is a resistor, a condenser, an IC, or the like. The sensor element 214 is an element which detects infrared rays necessary for measuring a temperature (body temperature) of a human body on which measurement is to be performed. Specifically, the sensor element 214 is a thermopile for detecting infrared rays emitted from the skin 10 and is an element which needs to be separated from the skin 10 by a certain distance.

Further, the sensor element 214 and the electronic component 213 are embedded in the resin substrate 212 and exposed from the substrate rear surface 212e. On the substrate rear surface 212e, exposed portions of the sensor element 214 and the electronic component 213 serve as electrodes. Also, the wiring 215 for electrically connecting the electrodes is formed on the substrate rear surface 212e.

Further, the sensor element 214 is embedded in the resin substrate 212 so that the substrate front surface 212c protrudes toward the front surface side of the contact-type sensor 200 further than the sensor element 214. That is, when the contact-type sensor 200 is brought into contact with the skin 10, the substrate front surface 212c protrudes toward the skin 10 side further than the sensor element 214.

Also, as illustrated in FIG. 2(b), in the contact-type sensor 200, a surface of both surfaces of the water absorptive sheet 211 on a side opposite to a surface thereof facing the substrate front surface 212c is used as a contact portion, and the contact portion is used by being brought into contact with the skin 10. At this time, a gap 200a is formed between the sensor element 214 and the skin 10.

Specifically, in the water absorptive sheet 211, an opening portion 211a is formed between the sensor element 214 and the skin 10, and in the resin substrate 212, a hollow portion 212a is formed between the sensor element 214 and the skin 10. Additionally, the opening portion 211a and the hollow portion 212a are aligned with the gap 200a.

When a surface of the sensor element 214 on a front surface side of the contact-type sensor 200 is defined as a sensor element front surface 214a, as illustrated in FIG. 2(b), the hollow portion 212a is formed to expose a part of the sensor element front surface 214a to the front surface side of the contact-type sensor 200, and the other portion (portion other than the above portion) of the sensor element front surface 214a is covered on the resin substrate 212. Therefore, by restricting the area of the hollow portion 212a to that with which only a necessary and sufficient amount of infrared radiation for measurement reaches the sensor element front surface 214a (detection surface), it is possible to prevent unnecessary substances from reaching the sensor element front surface 214a as much as possible.

Furthermore, in the embodiment, when a portion of the resin substrate 212 which faces a part of the sensor element front surface 214a is a facing portion 212d, the facing portion 212d is in a form of being in contact with the sensor element front surface 214a, but a gap may be formed between the facing portion 212d and the sensor element front surface 214a.

Subsequently, the contact-type sensor 200 of the embodiment will be described together with a manufacturing process thereof.

Process A

First, a process A is performed. The process A is a process of forming the resin substrate 212 on which the electronic component 213, the sensor element 214, the wiring 215 and the insulating layer 216 are mounted.

First, the resin substrate 212 in which the electronic component 213 and the sensor element 214 are embedded is formed by insert molding. The electronic components 213 and the sensor element 214 are embedded in the resin substrate 212 by insert molding and exposed from the substrate rear surface 212e.

Further, by the insert molding, the hollow portion 212a is formed so that the sensor element 214 is exposed from the substrate front surface 212c side (that is, the hollow portion 212a is formed in a region of the resin substrate 212 located between the skin 10 and the sensor element 214).

In other words, the hollow portion 212a is a concave portion formed on the substrate front surface 212c side of the resin substrate 212, a bottom surface of the concave portion corresponds to the sensor element front surface 214a, and a side surface of the concave portion is the facing portion 212d in FIG. 2(b).

Next, on the substrate rear surface 212e side, the wiring 215 which connects the electrodes of each electronic component 213 (or the electrodes of the electronic component 213 and the sensor element 214) is formed. In addition, the wiring 215 is a print wiring (printed wiring).

Next, the insulating layer 216 covering the substrate rear surface 212e is formed. As the insulating layer 216, an insulating resin can be used. As the insulating resin, for example, (1) a modified acrylate resist such as urethane acrylate, or (2) a soft coating material such as a polyester elastomer or olefin elastomer can be used.

Further, a portion of the electronic component 213 and the sensor element 214 exposed from the substrate rear surface 212e, and the wiring 215 are also covered with the insulating layer 216. As a result, as illustrated in FIG. 2(b), the wiring 215 and the electronic component 213 are sealed with the resin substrate 212 and the insulating layer 216.

In this way, the electronic component 213 and the sensor element 214 are embedded in the resin substrate 212, and the wiring 215 and the insulating layer 216 are provided on the substrate rear surface 212e of the resin substrate 212. Further, the process A can be realized by using the technique proposed in Patent Literature 3 (Japanese Patent No. 5359550).

The resin substrate 212 is manufactured by adding a water repellent additive to a resin base material. In the embodiment, PC (polycarbonate) is used as a base material, a fluorine-based surfactant (trade name: Surflon: AGC Seimi Chemical Co., Ltd.) is used as a water repellent additive, and the resin substrate 212 is manufactured by adding about 1 wt % of a fluorine-based surfactant to PC. Therefore, the resin substrate 212 becomes a water repellent substrate (water repellent portion, water repellent layer) having water repellency.

Further, in addition to PC, PE (polyester), PA (polyamide), PPC (polyphenylene sulfide), PP (polypropylene), elastomers or the like may be used as the base material used for the resin substrate 212. Also, as the water repellent additive used for the resin substrate 212, silicon-based pellets may be used in addition to the fluorine-based surfactant.

Furthermore, an amount of the water repellent additive added to the base material is set to an appropriate value in a range of 1 to 5 wt % according to a type of the base material and the water repellent additive.

Process B

The process A is followed by a process B. The process B is a process of covering the resin substrate 212, in which the electronic component 213 and the sensor element 214 are embedded, with the water absorptive sheet 211 and the hygroscopic sheet 217.

Specifically, the water absorptive sheet 211 and the hygroscopic sheet 217 which are larger in area than each of the substrate front surface 212c and the substrate rear surface 212e and also have substantially rectangular shapes are prepared. Additionally, as illustrated in FIG. 2(a) and FIG. 2(b), the absorptive sheet 211 is disposed to face the substrate front surface 212c, the hygroscopic sheet 217 is disposed to face the insulating layer 216, and an end of the water absorptive sheet 211 and an end of the hygroscopic sheet 217 are adhered to each other. The resin substrate 212 is placed inside a bag formed of the water absorptive sheet 211 and the hygroscopic sheet 217 so that the absorptive sheet 211 covers the substrate front surface 212c and the hygroscopic sheet 217 covers the insulating layer 216 formed on the substrate rear surface 212e.

The water absorptive sheet 211 is positioned between the skin 10 and the resin substrate 212 when the contact-type sensor 200 is in use and is in contact with the skin 10. As the water absorptive sheet 211, a material with good water absorptiveness such as a cloth material (for example, a cloth material having a structure having gaps between fibers such as gauze or the like), a sponge, or a foamed resin is used. Therefore, while the contact-type sensor 200 is in contact with the skin 10, liquid sweat generated from the skin 10 is absorbed into the water absorptive sheet 211.

Further, as the water absorptive sheet 211, a sponge material such as a urethane-based material may be used, and a foamed resin material may be used. A sheet obtained by applying a gel material (gel material capable of absorbing moisture of several hundred times the weight of the gel material itself) on a nonwoven fabric or the like can also be used as the water absorptive sheet 211.

Since the hygroscopic sheet 217 is positioned on an opposite side (rear surface side) to a side in contact with the skin 10 in the contact type sensor 200, it is preferable that the hygroscopic sheet 217 has a superior function of absorbing sweat vapor evaporated from the skin 10. Therefore, as the hygroscopic sheet 217, natural fiber (cotton, hemp, silk, or the like) having good hygroscopicity or regenerated fiber (rayon or the like) is used.

After the resin substrate 212 is wrapped with the water absorptive sheet 211 and the hygroscopic sheet 217, the opening portion 211a is formed in a portion of the water absorptive sheet 211 which faces the hollow portion 212a and the sensor element 114.

Figure 3:
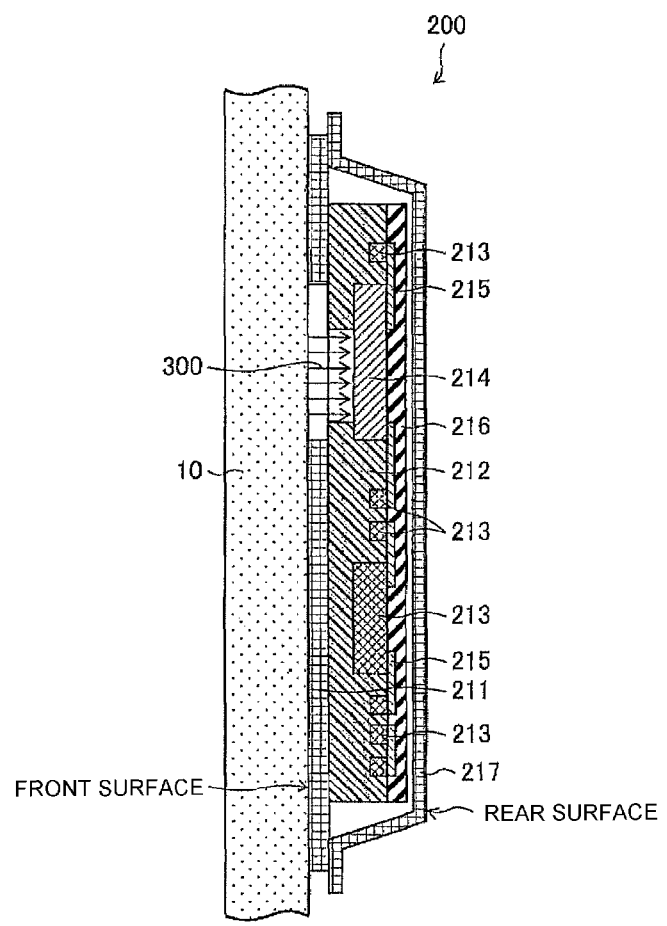
FIG. 3 is a view illustrating a state in which infrared radiation emitted from the skin is directed toward a sensor element of the contact-type sensor of FIG. 2.

Therefore, as illustrated in FIG. 3, when the water absorptive sheet 211 of the contact-type sensor 200 is brought into contact with the skin 10, the sensor element 214 is disposed at a portion spaced apart from the skin 10 at a predetermined distance, and the gap 200a is formed between the sensor element 214 and the skin 10. Accordingly, in the gap 200a, infrared rays 300 are generated from the skin 10, and the infrared rays 300 reach the sensor element front surface 214a (detection surface), and thus a body temperature is measured.

Also, since the measurement is performed as described above, in the contact-type sensor 200 of the embodiment, it is necessary to form the gap 200a between the sensor element 214 and the skin 10, and also it is not possible to perform sealing for providing waterproofing with respect to the gap 200a.

Therefore, as described above, the contact-type sensor 200 of the embodiment includes (a) the contact portion (water absorptive sheet 211) which is brought into contact with the skin 10 to be measured, (b) the sensor element 214 which is disposed with the gap 200a between the sensor element 214 and the skin 10 and detects the infrared rays (detection target) 300 generated from the skin 10 when the water absorptive sheet 211 is in contact with the skin 10, and (c) a water repellent portion (water repellent layer) and a water absorbing portion (water absorbing layer) which surrounds the gap 200a together with the skin 10 and the sensor element 214 when the water absorptive sheet 211 is in contact with the skin 10. Also, the resin substrate 212 serves as the water repellent portion, and the water absorptive sheet 211 serves as the water absorbing portion.

Figure 4A:
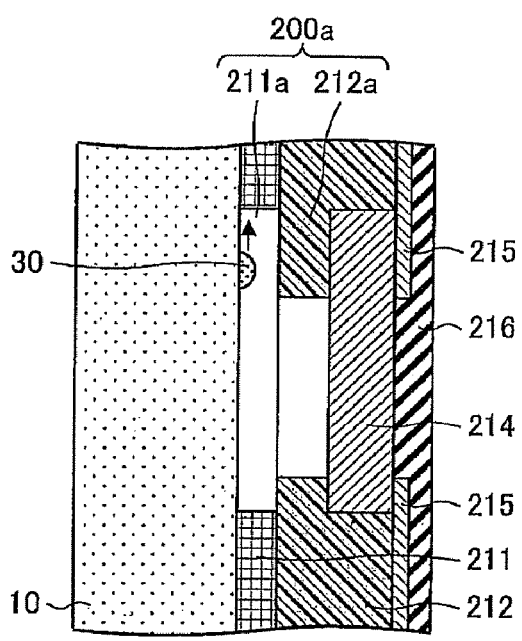
FIG. 4(*a*) and FIG. 4(*b*) are respectively a view illustrating a state in which a liquid enters a gap between the sensor element and the skin.
Figure 4B:
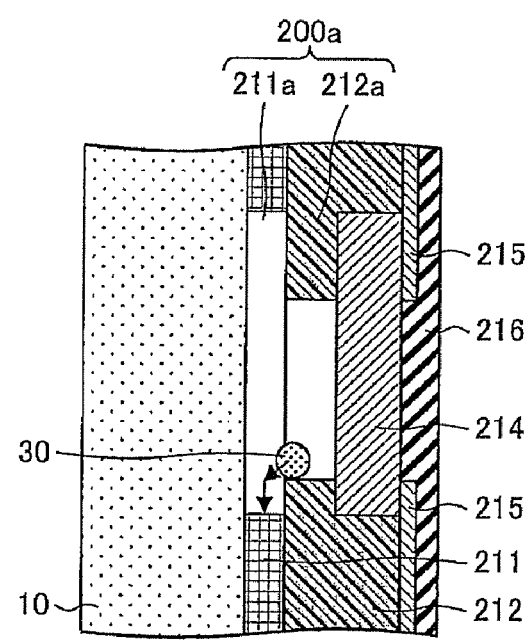

Therefore, even when a liquid (for example, sweat in a liquid state) enters the gap 200a between the skin 10 and the sensor element 214, (1) as illustrated in FIG. 4(a), the liquid 30 is absorbed by the water absorbing portion formed of the water absorptive sheet 211 by a capillary phenomenon, or (2) as illustrated in FIG. 4(b), the liquid 30 is repelled by a water repellent effect of the water repellent portion (the resin substrate 212) and is absorbed by the water absorbing portion (the water absorptive sheet 211).

Accordingly, since it is possible to prevent the liquid from reaching the sensor element 214 even when the liquid (for example, sweat in the liquid state) enters the gap 200a between the skin 10 and the sensor element 214 from the opening portion 211a, it is possible to prevent a problem (measurement error and breakage of internal elements) caused by the liquid being attached to the sensor element 214.

In addition, in the contact-type sensor 200 of the embodiment, the electronic component 213 and the wiring 215 are sealed with the resin substrate 212 and the insulating layer 216. That is, the electronic component 213 and the wiring 215 are surrounded by the resin substrate 212 and the insulating layer 216 without a gap so as not to be in contact with external air. Therefore, the electronic component 213 and the wiring 215 are shielded from water or moisture in the air, and a waterproofing effect with respect to the electronic component 213 and the wiring 215 can be obtained.

Further, according to in the contact-type sensor 200 of the embodiment, the substrate front surface 212c is covered with the water absorptive sheet 211, and the water absorptive sheet 211 is brought into contact with the skin 10 to be measured, and the measurement is performed. In the contact-type sensor 200, since the water absorptive sheet 211 is in contact with the skin 10, the sweat generated from the skin is absorbed by the water absorptive sheet 211 at a contact portion, and inhibition of perspiration from the skin is suppressed, and occurrence of dermatitis caused by the inhibition of the perspiration can be suppressed. On the other hand, in the conventional contact-type sensor, since a contact surface with the skin is formed of a material having no water absorbing function, there is a problem that perspiration from the skin is inhibited and thus dermatitis due to the inhibition of the perspiration occurs.

Further, according to in the contact-type sensor 200 of the embodiment, since the resin substrate 212 is covered with the water absorptive sheet 211 and the hygroscopic sheet 217, there is an effect of improving waterproofing of the sensor element 214 and the electronic component 213 mounted on the resin substrate 212.

Also, in the embodiment, the thermopile is used as the sensor element 214, but there is no limitation to a thermopile as long as there is a sensor element used at a certain distance from the skin 10.

For example, as the sensor element 214, an electronic polymer type, a resistance change type, or a capacitance change type humidity sensor can be used. In this case, the sensor element 214 detects the sweat vapor generated from the skin 10, and the contact-type sensor 200 serves as a perspiration measuring device which measures a degree of the perspiration. Additionally, in the contact-type sensor 200, since the gap 200a (a space hardly affected by an external environment) is formed between the skin 10 and the sensor element 214 and the gap 200a is surrounded by the water repellent portion and the water absorbing portion, even when a humidity sensor is used as the sensor element 214, a liquid (for example, sweat in a liquid state) is attached to the sensor element 214 can be suppressed while a space required for measurement is formed between the sensor element 214 and the skin 10.

Modified Example

In the above-described embodiment, although the electronic component 213 and the sensor element 214 are embedded in the resin substrate 212 using the method disclosed in Patent Document 3 (Japanese Patent No. 5359550), a method other than the method of Patent Document 3 may be used. For example, a well-known method of manufacturing a printed circuit board can be used. This point will be described with reference to FIG. 5(a) to FIG. 5(c).

Figure 5A:
FIG. 5(*a*), FIG. 5(*b*) and FIG. 5(*c*) are respectively a cross-sectional view illustrating a manufacturing process of a contact-type sensor according to a modified example.
Figure 5B:
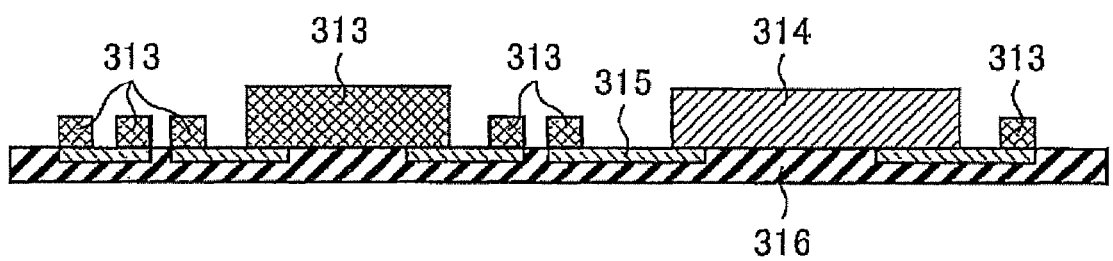
Figure 5C:
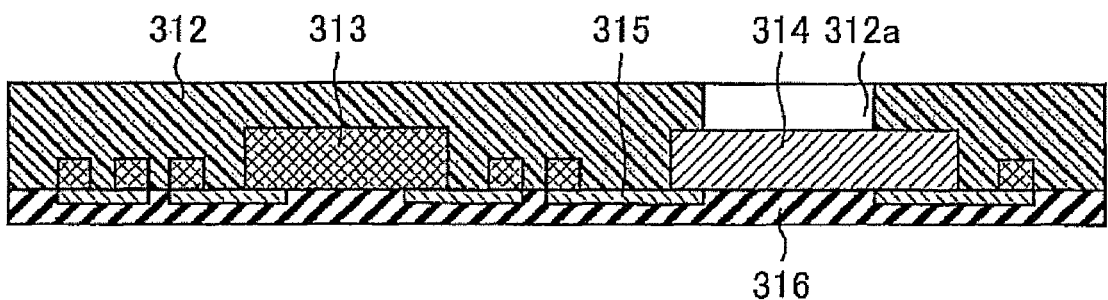

First, as illustrated in FIG. 5(a), a printed circuit in which a copper wiring 315 is formed on one surface of an insulating layer (insulating substrate) 316 formed of a polyimide resin is manufactured. Subsequently, as illustrated in FIG. 5(b), on a surface of the insulating layer 316 on a side in which the copper wiring 315 is formed, an electronic component 313 (resistor, condenser, IC) and a sensor element 314 are mounted by soldering or the like. Subsequently, as illustrated in FIG. 5(c), a resin substrate 312 is formed on a surface of the insulating layer 316 on the side on which the copper wiring 315, the electronic component 313 and the sensor element 314 are mounted.

Specifically, the resin substrate 312 is formed on the insulating layer 316 so that the copper wiring 315 and the electronic component 313 are sealed with the resin substrate 312 and the insulating layer 316 and a hollow portion 312a which exposes a side of the sensor element 314 opposite to a side in contact with the insulating layer 316 is formed. Also, like the resin substrate 212, the resin substrate 312 is prepared by adding a water repellent additive to a base material formed of a resin.

After that, the process B is performed in the same manner as in the previously described embodiment.

In the above embodiment, an example in which the contact-type sensor is used in contact with the human skin has been described, but it is obvious that it is not limited to the human skin but applicable to the skin of animals in general.

The present invention is not limited to each of the above-described embodiments, and various modifications are possible within the range indicated in the claims, and embodiments obtained by appropriately combining technical means disclosed in different embodiments are also included in the technical scope of the present invention.

Summary

As described above, the contact-type sensor of the present invention includes a contact portion which is brought into contact with an object to be measured, a sensor element which is disposed with a gap between the sensor element and the object to be measured and detects a detection target generated from the object to be measured when the contact portion is in contact with the object to be measured, and a water repellent portion and a water absorbing portion which surrounds the gap together with the object to be measured and the sensor element when the contact portion is in contact with the object to be measured.

According to the configuration of the present invention, even when a liquid flows into the gap, the liquid can be moved to the water absorbing portion by being repelled by the water repellent portion and then can be absorbed in the water absorbing portion. Therefore, it is possible to prevent the liquid from being attached to the sensor element, and thus it is possible to suppress the measurement error and the breakage of the element.

Also, in addition to the above-described configuration, the contact-type sensor of the present invention may include a water repellent substrate having the sensor element embedded therein and having a substrate front surface protruding to a side of the object to be measured further than the sensor element when the contact portion is in contact with the object to be measured, and a water absorptive sheet covering the substrate front surface and of which a surface on a side opposite to a surface facing the substrate front surface is the contact portion, and in the water repellent substrate, a hollow portion is formed in a region located between the sensor element and the object to be measured when the contact portion is in contact with the object to be measured, and in the water absorptive sheet, an opening portion may be foil led in a region located between the sensor element and the object to be measured when the contact portion is in contact with the object to be measured, and the gap may be the hollow portion and the opening portion, the water repellent portion may be the water repellent substrate, and the water absorbing portion may be the water absorptive sheet.

According to the configuration of the present invention, it is possible to realize the gap surrounded by the object to be measured, the sensor element, the water repellent portion and the water absorbing portion with a simple configuration, and thus there is an advantage that a contact-type sensor having such a configuration is easily manufactured.

Further, in addition to the above-described configuration, the contact-type sensor of the present invention may include a plurality of electronic components embedded in the water repellent substrate to be exposed from the substrate rear surface when a surface of the water repellent substrate on a side opposite to the substrate front surface is a substrate rear surface, a wiring which connects the electronic components to each other, and an insulating layer provided on the substrate rear surface to seal the wiring and the plurality of electronic components.

According to the configuration of the present invention, since the electronic component and the wiring can be prevented from being in contact with air, moisture in the air does not come into contact with the electronic component and the wiring, and a waterproof effect with respect to the electronic component and the wiring can be obtained.

Further, in the contact-type sensor of the present invention, in addition to the above-described configuration, the object to be measured may be a body surface, and the water absorptive sheet serving as the contact portion may be included.

According to the configuration of the present invention, sweat generated from the body surface (skin) at the contact portion between the body surface and the water absorptive sheet is absorbed by the water absorptive sheet, inhibition of perspiration from the skin is suppressed, and occurrence of dermatitis caused by the inhibition of the perspiration can be suppressed.

Also, in the contact-type sensor of the present invention, in addition to the above-described configuration, the object to be measured may be the body surface, and the sensor element may be a thermopile which detects infrared rays generated from the body surface as the detection target to measure a temperature of the body surface. Alternatively, in the contact-type sensor of the present invention, in addition to the above-described configuration, the object to be measured may be a body surface, and the sensor element may be a humidity sensor which detects sweat vapor generated from the body surface as the detection target to measure a degree of perspiration of the body surface.

What is claimed is:

1. A contact-type sensor configured to measure an object to be measured which is a body surface, comprising:
   a contact portion which is brought into contact with the object to be measured,
   a sensor element which is disposed with a gap between the sensor element and the object to be measured and detects a detection target generated from the object to be measured when the contact portion is in contact with the object to be measured,
   a water repellent substrate having the sensor element embedded therein and having a substrate front surface which protrudes to a side of the object to be measured further than the sensor element when the contact portion is in contact with the object to be measured, and
   a water absorptive sheet which covers the substrate front surface and a surface of the water absorptive sheet that is away from the substrate front surface is the contact portion,
   wherein the gap is enclosed by the water repellent substrate, the water absorptive sheet, the object to be measured, and the sensor element when the contact portion is in contact with the object to be measured,
   wherein the gap is constituted by a hollow portion of the water repellent substrate and an opening portion of the water absorptive sheet located between the sensor element and the object to be measured when the contact portion is in contact with the object to be measured, and
   wherein the water repellent substrate includes a resin base material treated with a water repellent additive, and the water absorptive sheet includes a material capable of absorbing liquid sweat generated by the object to be measured.

2. The contact-type sensor according to claim 1, further comprising a plurality of electronic components embedded in the water repellent substrate to be exposed from a substrate rear surface when a surface of the water repellent substrate on a side opposite to the substrate front surface is the substrate rear surface, a wiring which connects the electronic components to each other, and an insulating layer provided on the substrate rear surface to seal the wiring and the plurality of electronic components.

3. The contact-type sensor according to claim 2, wherein the sensor element is a thermopile which detects infrared rays generated from the body surface as the detection target to measure a temperature of the body surface.

4. The contact-type sensor according to claim 2, wherein the sensor element is a humidity sensor which detects sweat vapor generated from the body surface as the detection target to measure a degree of perspiration of the body surface.

5. The contact-type sensor according to claim 1, wherein the sensor element is a thermopile which detects infrared rays generated from the body surface as the detection target to measure a temperature of the body surface.

6. The contact-type sensor according to claim 1, wherein the sensor element is a humidity sensor which detects sweat vapor generated from the body surface as the detection target to measure a degree of perspiration of the body surface.

* * * * *